(12) United States Patent
Barnes et al.

(10) Patent No.: US 11,547,573 B2
(45) Date of Patent: Jan. 10, 2023

(54) EXPANDABLE INTERBODY IMPLANT WITH TEETH DRIVEN LINKAGES

(71) Applicant: K2M, Inc., Leesburg, VA (US)

(72) Inventors: Liam Patrick Barnes, Leesburg, VA (US); Clint Boyd, Leesburg, VA (US)

(73) Assignee: K2M, INC., Leesburg, VA (US)

( * ) Notice: Subject to any disclaimer, the term of this patent is extended or adjusted under 35 U.S.C. 154(b) by 0 days.

(21) Appl. No.: 17/223,517

(22) Filed: Apr. 6, 2021

(65) Prior Publication Data

US 2021/0315709 A1    Oct. 14, 2021

Related U.S. Application Data

(60) Provisional application No. 63/006,805, filed on Apr. 8, 2020.

(51) Int. Cl.
*A61F 2/44* (2006.01)

(52) U.S. Cl.
CPC ...... *A61F 2/4425* (2013.01); *A61F 2002/443* (2013.01)

(58) Field of Classification Search
CPC ......... A61F 2/4455–2/447; A61F 2002/30579; A61F 2/44; A61F 2/4425; A61F 2002/443; A61F 2002/30538; A61F 2002/30556
See application file for complete search history.

(56) References Cited

U.S. PATENT DOCUMENTS

| | | | |
|---|---|---|---|
| 7,087,055 B2 | 8/2006 | Lim et al. | |
| 7,824,445 B2 | 11/2010 | Biro et al. | |
| 8,366,777 B2* | 2/2013 | Matthis | A61F 2/4465 623/17.16 |
| 8,579,979 B2 | 11/2013 | Edie et al. | |
| 9,737,411 B2* | 8/2017 | Loebl | A61F 2/4455 |
| 10,137,006 B2* | 11/2018 | Dewey | A61F 2/4611 |
| 2003/0236520 A1* | 12/2003 | Lim | A61B 17/025 606/99 |
| 2007/0255415 A1* | 11/2007 | Edie | A61F 2/4611 623/17.16 |
| 2011/0160861 A1* | 6/2011 | Jimenez | F16H 25/20 623/17.16 |
| 2013/0158668 A1* | 6/2013 | Nichols | A61F 2/4611 623/17.16 |
| 2014/0194991 A1* | 7/2014 | Jimenez | A61F 2/4611 623/17.15 |
| 2016/0331542 A1* | 11/2016 | Faulhaber | A61F 2/447 |
| 2017/0056200 A1* | 3/2017 | Koch | A61F 2/4611 |
| 2017/0156885 A1* | 6/2017 | Zur | A61F 2/4611 |
| 2019/0091034 A1* | 3/2019 | Dewey | A61F 2/4425 |
| 2021/0315709 A1* | 10/2021 | Barnes | A61F 2/4425 |

FOREIGN PATENT DOCUMENTS

WO    9525485 A1    9/1995

* cited by examiner

*Primary Examiner* — Eduardo C Robert
*Assistant Examiner* — Michelle C Eckman
(74) *Attorney, Agent, or Firm* — Duane Morris LLP

(57) ABSTRACT

A spinal interbody implant includes a shaft extending along and rotatable about a central axis. The shaft includes a first threaded region. The implant further includes a first link having a first end with first gear teeth. The first end of the first link is fixed at a first point relative to the central axis such that the first gear teeth engage the first threaded region.

16 Claims, 5 Drawing Sheets

EXPANDABLE INTERBODY IMPLANT WITH TEETH DRIVEN LINKAGES

This application claims the benefit of U.S. Provisional Application No. 63/006,805, filed on Apr. 8, 2020, the disclosure of which is hereby incorporated herein by reference.

BACKGROUND

Intervertebral implants are commonly used in spinal surgery, such as in interbody fusion procedures, in which an implant (e.g., a spacer or cage) is placed in the disc space between two vertebrae to be fused together. At least a portion of the disc is typically removed before the implant is positioned in the intervertebral space, and the implant may be supplemented with bone graft material to promote fusion of the vertebrae. Interbody fusion procedures may also be performed in conjunction with other types of fixation, such as pedicle screw fixation, to provide additional stability, particularly while the vertebrae fuse together.

Some such intervertebral implants often have an initially contracted configuration, such that they have a low profile in the superior-inferior direction, in order to ease insertion into the intervertebral space. Such expandable implants can then be expanded in the superior-inferior direction after implantation, so as to securely engage and stabilize the vertebrae on both sides of the intervertebral space.

BRIEF SUMMARY

The present disclosure relates to an implant that may have a contracted closed position and an expanded open position. The implant may include a shuttle extending along a central axis and one or more endplates disposed around the shuttle. The one or more endplates may be moveable from the closed position to the open position such that the endplates are further from the central axis than in the closed position. One or more rows of links may connect the endplates to the shuttle. The links may each have a shuttle end rotatably fixed to the shuttle at an immovable location such that the shuttle ends cannot translate relative to the central axis.

A shaft may extend within the shuttle and along the central axis such that the shaft is rotatable relative to the shuttle about the central axis. The shaft may have a worm threaded region in geared engagement with gear teeth extending from the shuttle ends of at least some of the links. Rotationally driving the shaft may thereby cause the links to pivot. Pivoting of the links driven by the shaft may cause the endplates to move to or from the open position.

In another aspect, a spinal interbody implant may include a shaft extending along and rotatable about a central axis. The shaft may include a first threaded region. The implant may further include a first link having a first end with first gear teeth. The first end of the first link may be fixed at a first point relative to the central axis such that the first gear teeth engage the first threaded region.

In some arrangements according to any of the foregoing, the spinal interbody implant may include an endplate, and the first link may include a second end connected to the endplate.

In some arrangements according to any of the foregoing, the spinal interbody implant may include a second threaded region located at a different position along the central axis than the first threaded region. The implant may include a second link having a first end having second gear teeth and being fixed at a second point relative to the central axis such that the second gear teeth engage the second threaded region and such that the second link may rotate about the second point.

In some arrangements according to any of the foregoing, the spinal interbody implant may include an endplate, and wherein the first link includes a second end connected to the endplate.

In some arrangements according to any of the foregoing, the spinal interbody implant may be transitionable from a closed position to an open position. The closed position the first link and the second link may each extend in generally the same direction relative to the central axis.

In some arrangements according to any of the foregoing, the links may extend proximally away from their first ends in the closed position.

In some arrangements according to any of the foregoing, the links may extend perpendicularly relative to the central axis in the open position.

In some arrangements according to any of the foregoing, the shaft may be nontranslatably retained within a cavity of a shuttle. The first end of the first link may be fixed to the shuttle.

In some arrangements according to any of the foregoing, the implant may include a plurality of endplates moveable between a closed position wherein the endplates contact the shuttle and an open position wherein the endplates are spaced apart from the shuttle.

In some arrangements according to any of the foregoing, the endplates may be located at a different location along the central axis in the open position than in the closed position.

In some arrangements according to any of the foregoing, the first link may include a second end connected to one of the endplates.

In some arrangements according to any of the foregoing, the endplates may be equally spaced around the central axis in both the open position and the closed position.

In some arrangement according to any of the foregoing s, the endplates may meet in the closed position to form a rounded nose at a distal end of the implant.

In some arrangements according to any of the foregoing, the endplates may meet in the closed position to form a generally enclosed capsule shape from a distal tip of the nose to proximal ends of the endplates.

In another aspect, a spinal interbody implant may include a shuttle extending along a central axis. A plurality of endplates may be spaced circumferentially around the central axis and the shuttle. A first plurality of links may be connected at a geared first end to the shuttle at a fixed location relative to the central axis and may be connected at a second end to one of the endplates. A shaft may be disposed within the shuttle and along the central axis and including a first threaded region in geared engagement with the first ends of the first plurality of links. A first plurality of links are drivable by rotation of the shaft to transition the implant from a closed position to an open position. The first plurality of links may extend at a greater angle relative to the central axis in the open position than in the closed position.

In some arrangements according to any of the foregoing, the endplates may be spaced further from the central axis in the open position than in the closed position.

In some arrangements according to any of the foregoing, the implant may include a second plurality of links. Each link of the second plurality of links may be connected at a geared first end to the shuttle at a fixed location relative to the central axis and connected at a second end to one of the endplates. The shaft may include a second threaded region in geared engagement with the first ends of the second plurality of links. Each of the endplates may be connected to a second end of at least one link of the first plurality of links and at least one link of the second plurality of links.

In some arrangements according to any of the foregoing, the second ends of the first plurality of links may be further from the second ends of the second plurality of links in the open position than in the closed position.

In some arrangements according to any of the foregoing, the endplates may include elongate tracks and the second ends of the first plurality of links are translatably connected to the endplates within the tracks.

In another aspect, a method of treating a spinal injury may include inserting an implant between two vertebrae. The implant may include a shaft extending along a central axis. The shaft may include a first threaded region and a driveable end. The implant may further include a first link having a first end with first gear teeth. The first end of the first link may be fixed at a first point relative to the central axis such that the first gear teeth engage the first threaded region. The method may further include rotating the first link about the first point by driving the shaft with a tool engaged to the driveable end.

In some arrangements according to any of the foregoing, the implant may include an endplate and the first link may includes a second end fixed to the endplate such that rotating the first link about the first point moves the endplate relative to the central axis.

In some arrangements according to any of the foregoing, the implant may include a second link having a first end with second gear teeth. The first end of the second link may be fixed at a second point relative to the central axis, and the shaft may include a second threaded region engaged with the second gear teeth such that the driving of the shaft causes the second link to rotate about the second point.

In some arrangements according to any of the foregoing, the implant may include an endplate and the first link and the second link each include a second end fixed to the endplate such that rotating the first link and second link about the first point and second point, respectively, causes the endplate to translate relative to the central axis.

DETAILED DESCRIPTION

When referring to specific directions and planes in the following disclosure, it should be understood that, as used herein, the term "proximal" means closer to the operator/surgeon, and the term "distal" means further away from the operator/surgeon. The term "anterior" means toward the front of the body or the face, and the term "posterior" means toward the back of the body. With respect to the longitudinal axis of the spine, the term "superior" refers to the direction towards the head, and the term "inferior" refers to the direction towards the pelvis and feet. The "transverse plane" is that plane which is orthogonal to the longitudinal axis of the spine. The "coronal plane" is a plane that runs from side to side of the body along the longitudinal axis of the spine and divides the body into anterior and posterior portions. The "sagittal plane" is a plane that runs along the longitudinal axis of the spine and defines a plane of symmetry that separates the left and right sides of the body from each other. Finally, the "medial" refers to a position or orientation toward the sagittal plane, and lateral refers to a position or orientation relatively further from the sagittal plane.

Figure 1A:
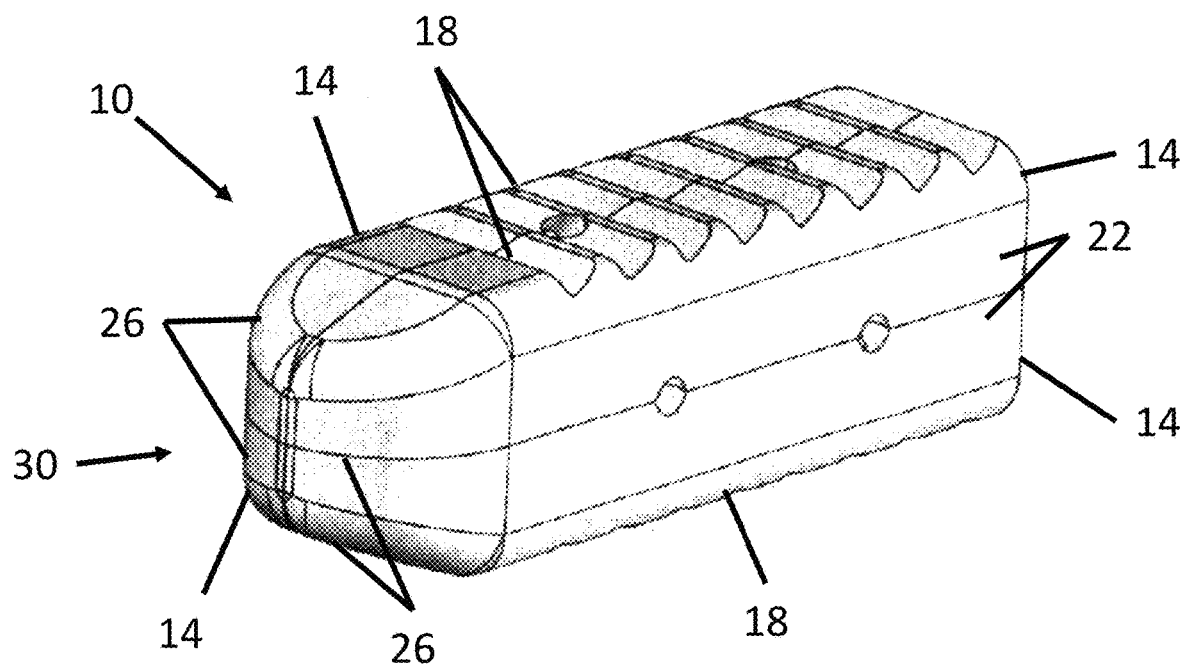
FIG. 1A is a top perspective view of an implant according to a first arrangement in a closed position.
Figure 1B:
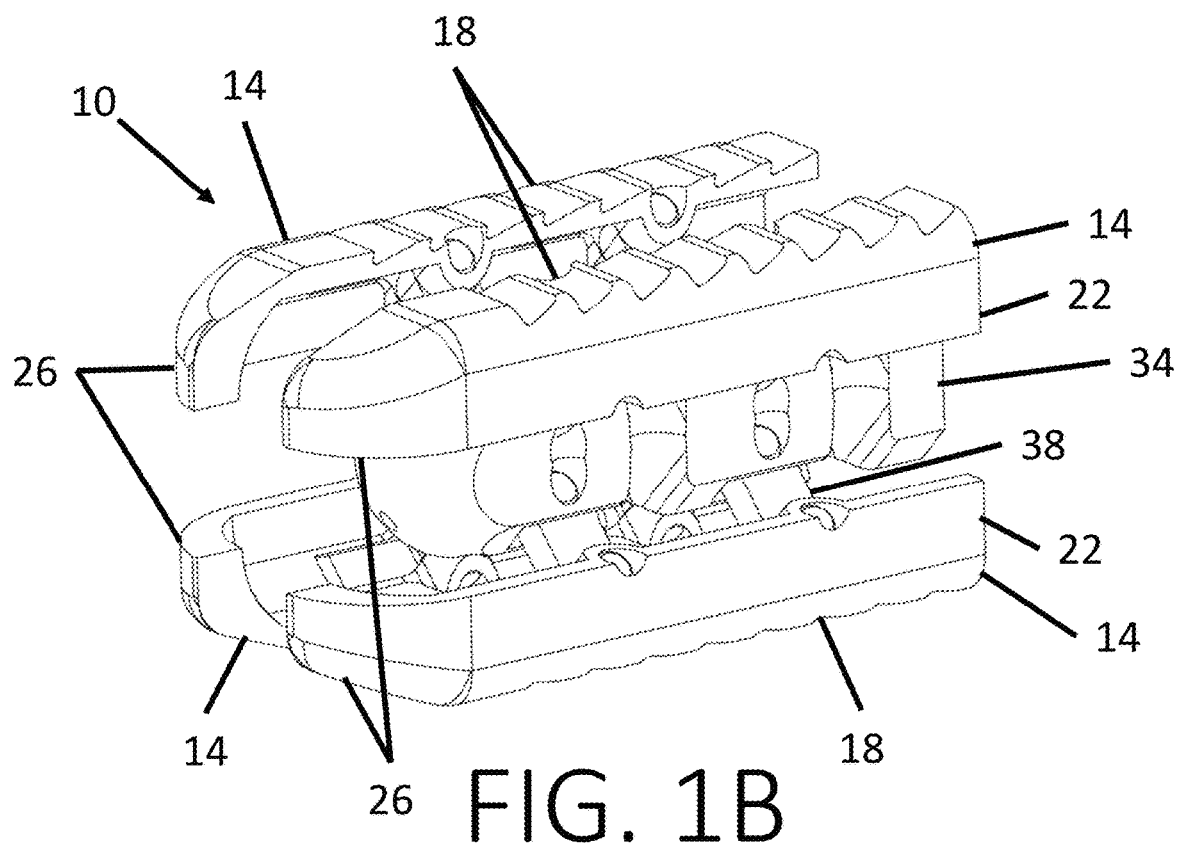
FIG. 1B is a top perspective view of the implant of FIG. 1A in an open position.

An interbody implant 10 is shown in a closed position in FIG. 1A and an open position in FIG. 1B. The implant includes four elongate endplates 14 that meet in generally the shape of a right rectangular prism in the closed position. Each endplate 14 includes a ridged exterior surface 18 and an exterior flat surface 22, with the ridged exterior surface 18 of each endplate 14 extending generally along a plane that is perpendicular to the flat exterior surface 22 of the same endplate. The endplates 14 are arranged so that the ridged surface 18 of each endplate is adjacent to a ridged surface 18 of another endplate 14, and the flat surface 22 of each endplate 14 is adjacent to a flat surface 22 of another endplate 14. The ridged surfaces 18 are configured to facilitate engagement with adjacent vertebrae, so in some examples the implant 10 is implanted within a patient such that the ridged surfaces 18 extend parallel to the transverse plane of a patient and the flat surfaces 22 extend perpendicular to the transverse plane of the patient. Corners formed where the ridged surface 18 and flat surface 22 of each endplate meet provide the long edges of the rectangular prism shape of the implant 10 in the closed position. In other arrangements, the endplates may instead include only flat or only ridged exterior surfaces, or may have arcuate exterior surfaces such that the closed position of the implant 10 has a generally cylindrical shape.

Each endplate includes a contoured distal portion 26. In the closed position shown in FIG. 1A, the contoured distal portions 26 of the four endplates meet to provide a smooth nose 30 at a distal end of the implant 10. The nose's 30 smooth surface allows the implant 10 to be advanced distally through soft tissue and between the adjacent vertebral bodies with more ease and less trauma than a flat end. In the closed position, edges of the endplates 14 meet or come close to meeting along a distal to proximal length of the implant 10 to provide a generally continuous capsule shape from a distal tip of the nose 30 to the proximal ends of the endplates 14.

In the open position shown in FIG. 1B, the endplates 14 are expanded outward relative to a shuttle 34 extending lengthwise within the implant 10. The endplates 14 are supported in an X shape and connected to the shuttle 34 by rigid links 38.

Figure 2A:
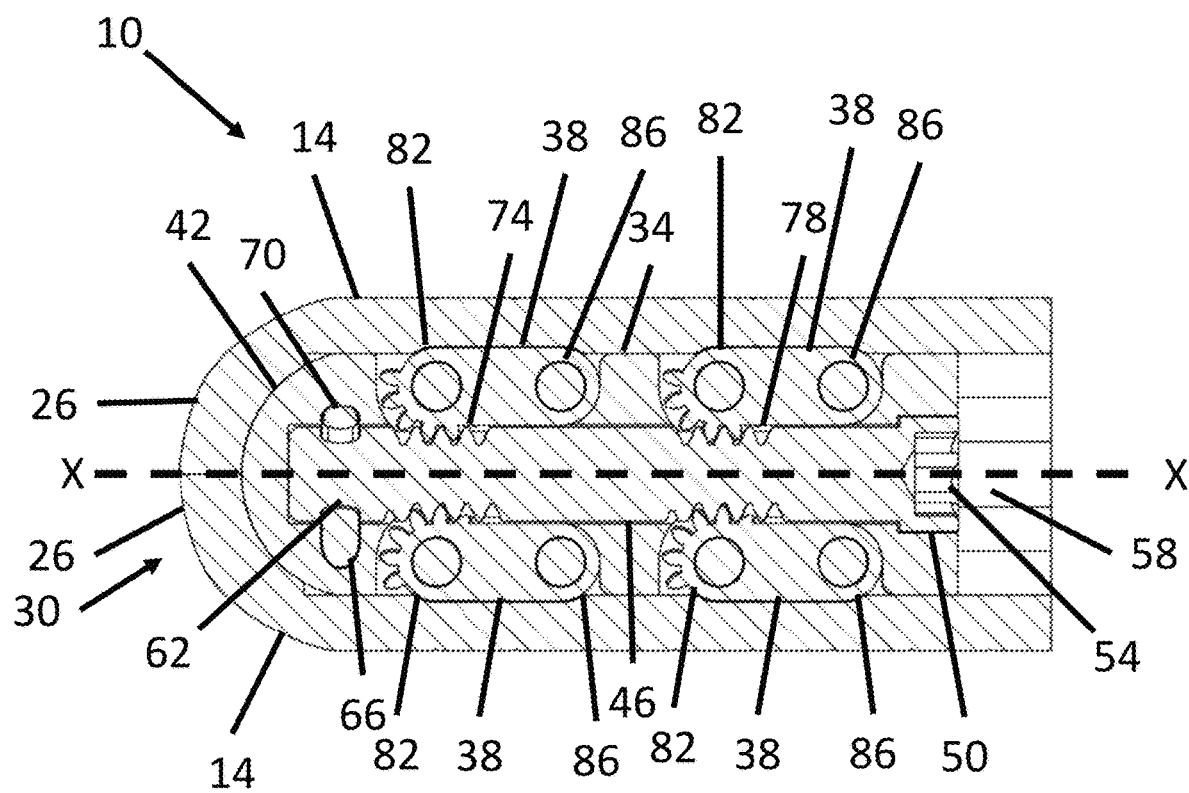
FIG. 2A is a side elevation section view of the implant of FIG. 1A in the closed position.
Figure 2B:
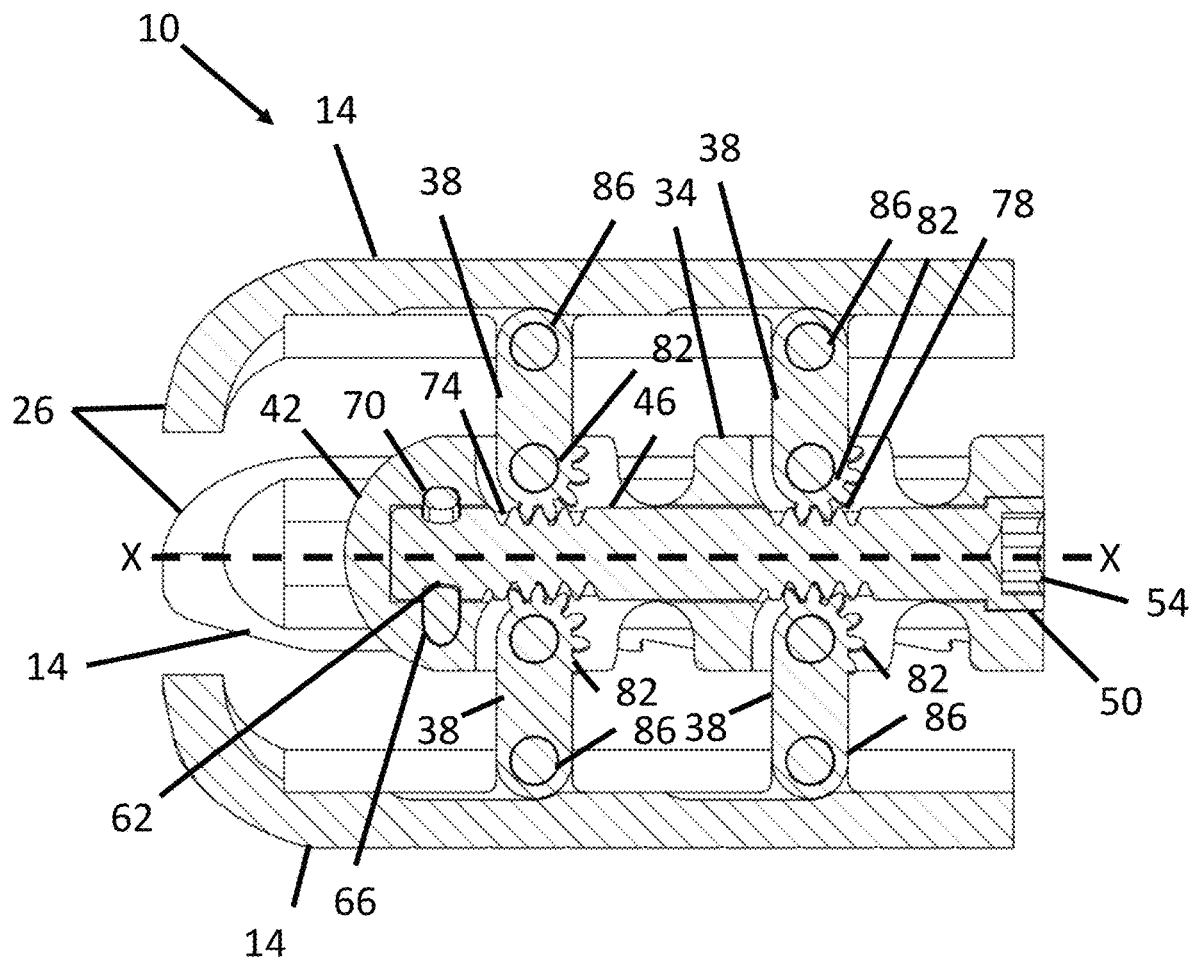
FIG. 2B is a side elevation section view of the implant of FIG. 1A in the open position.

As shown in FIGS. 2A and 2B, the shuttle 34 is centered between the endplates 14 to extend along a central longitudinal axis X of the implant. A dome 42 provides a distal end of the shuttle 34. In the closed position, the dome 42 nests within round interior contours of the distal portions 26 of the endplates 14. A shaft 46 is centered within the shuttle 34 and extends within the shuttle 34 from within the dome 42 to a proximal end of the shuttle 34. The shaft 46 is generally cylindrical in shape and is disposed within an internal cavity of the shuttle 34 that is closely fitted to the shaft 46. The close fit of the internal cavity allows the shaft 46 to rotate about the central axis X while maintaining the shaft 46 in alignment with the central axis X.

In the illustrated arrangement, a flared end 50 provides a proximal end of the shaft 46, but in other arrangements the proximal end of the shaft 46 is of equal or lesser diameter than an adjoining part of the shaft 46. The proximal end of the shaft 46 includes a drivable feature 54, which is a recess having teeth for engaging with a driving tool. In other arrangements, the drivable feature 54 is a toothed protrusion or any other rotatably drivable element. The drivable feature 54 is accessible from a proximal end of the implant 10 through a proximal space 58 defined within the endplates 14 in the closed position.

The shaft 46 includes a neck 62 disposed proximate (e.g., within) the dome 42. The neck 62 is a region of the shaft 42 having a smaller diameter than a distally adjacent region of the shaft 42. The neck 62 is aligned with a channel 66 intersecting the cavity within the shuttle 34 and extending perpendicularly to the longitudinal axis X. A clip 70 is disposed within the channel 66 and extends into the neck 62. The channel 66 and clip 70 have equal thicknesses along the direction of the central axis X, so the clip 70 abuts both proximal and distal sides of the channel 66 and a distal end of the neck 62. The clip 70 thereby prevents the shaft 46 from moving proximally within the shuttle 34. The shaft 46 is also prevented from moving distally within the shuttle 34 because the clip 70 abuts a distal end of the neck 62 and because a distal end of the shaft 46 abuts a proximal end of the cavity. The interaction between the flared end 50 of the shaft 46 and the shuttle 34 may also prevent the shaft 46 from moving distally within the shuttle 34. In other arrangements, distal travel of the shaft 46 is limited only by the clip 70 or the distal end of the cavity or the flared end 50 of the shaft 46. The limitations on the proximal and distal travel of the shaft 46 within the shuttle 34 cooperate to substantially or entirely prevent axial travel of the shaft 46 within the shuttle 34.

The shaft includes a distal threaded region 74 and a proximal threaded region 78. The threaded regions 74, 78 are both worm threaded in the same direction and engage teeth extending from a shuttle end 82 of each link 46. The gear teeth of the shuttle ends 82 of the illustrated arrangement are helical, and therefore extend transverse to pivot axes 82 of their respective shuttle ends 82, but in other arrangements the gear teeth may be parallel to the pivot axes of their respective shuttle ends 82. In the illustrated arrangement, the threaded regions 74, 78, are separated by an unthreaded section of the shaft 46, but in other arrangements the threaded regions 74, 78 are contiguous. In yet further arrangements, the shaft 46 includes only one threaded region. The shuttle end 82 of each link 46 is rotatably connected at a fixed location to the shuttle 34 such that gear teeth extending radially outward from the shuttle end 82 may engage one of the threaded regions 74, 78. Teeth extend from a portion of the perimeter of the shuttle ends 82 such that the teeth continuously engage the threaded regions 74, 78 from the closed position of the implant 10 to the open position of the implant 10. The links 38 may therefore be driven between the open position and the closed position by rotation of the shaft 46 within the shuttle 34. Turning the shaft 46 within the shuttle causes the worm threading of the threaded regions 74, 78 to act on the teeth of the shuttle ends 82 of the links 46, which causes the links 46 to pivot in unison about the shuttle ends 82 relative to the shuttle.

In the closed position shown in FIG. 2A, the endplates 14 contact the shuttle 34 and the links 38 each extend proximally from their shuttle end 82 parallel to the central axis X. The links 38 therefore extend in the same, or at least generally the same, direction as one another with respect to the central axis X away from their respective shuttle ends 34. In other arrangements, the links 38 extend at nonzero acute angles with respect to the central axis X in the closed position. In the open position shown in FIG. 2B, the endplates 14 do not contact the shuttle and the links 38 each extend perpendicularly away from the central axis X and away from their respective shuttle ends 82. The links 38 therefore extend in the same direction as one another relative to the central axis X in the open position as well. In other arrangements, the links 38 merely extend at a greater angle relative to the central axis X in the open position than the closed position. In both the open position and the closed position, the endplates 14 are equally spaced around the central axis X.

The links 38 in the illustrated arrangement rotate 90° between the open position and the closed position of the implant 10. However, in other arrangements, the shuttle ends 82 are threaded across a broader or narrower range, and the links 38 are configured to rotate across a greater angle between the open position and the closed position. For example, in some arrangements, the links 38 in the closed position extend distally from the shuttle ends 82, or slightly toward or slightly away from the central axis X. In further arrangements, the links 38 extend distally or proximally in the open position. In yet further arrangements, only one link 38 per endplate 14 has a toothed shuttle end 82.

The angle between the links 38 and the central axis X for the open position may be dictated by geometry of the shuttle 34, such as by ridges or stops adjacent to the shuttle ends 82 preventing rotation beyond a certain range. The implant 10 is configured such that its structures and internal friction prevent collapse from the open position to the closed position after the implant 10 is implanted between two vertebrae. Specifically, the implant 10 is constructed such that expected loads from two adjacent vertebrae between which the implant may be implanted will not force the implant 10 to collapse from the open position to the closed position. In some arrangements, collapse is prevented by the open position being defined by an ultimate position reached by the links 38 after travelling to or past a 90° angle to the central axis X.

Each link 38 includes a plate end 86 opposite from shuttle end 82. Each plate end 86 is rotatably connected at a fixed location to an interior side of an endplate 14. The above described rotational driving of the links 38 between the open and closed positions thus moves the endplates 14 between the open and closed positions. In the illustrated arrangement, two links 38 are connected to each endplate 14, meaning the implant 10 includes eight links 38 in total. In various other arrangements, more or fewer links 38 are connected to each endplate 14.

Because the shuttle ends 82 cannot translate relative to the shuttle 34 and the endplate ends 86 cannot translate relative to their respective endplates 14, the rotation of the links 38 caused by turning the shaft 46 moves the endplates 14 both axially and radially relative to the central axis X. In the illustrated example, the endplates 14 travel distally relative to the central axis X as the implant 10 expands from the closed position to the open position. The distal travel of the endplates 14 causes the proximal end of the shuttle 34 to extend proximally beyond the endplates 14 and causes the distal portions 26 of the endplates 14 to be spaced distally away from the dome 42 when the implant 10 is in the open position. In other arrangements, the links 38 extend distally from the shuttle ends 82 when the implant 10 is in the closed position, so the endplates 14 travel proximally relative to the shuttle 34 as the implant 10 expands to the open position.

Figure 3:
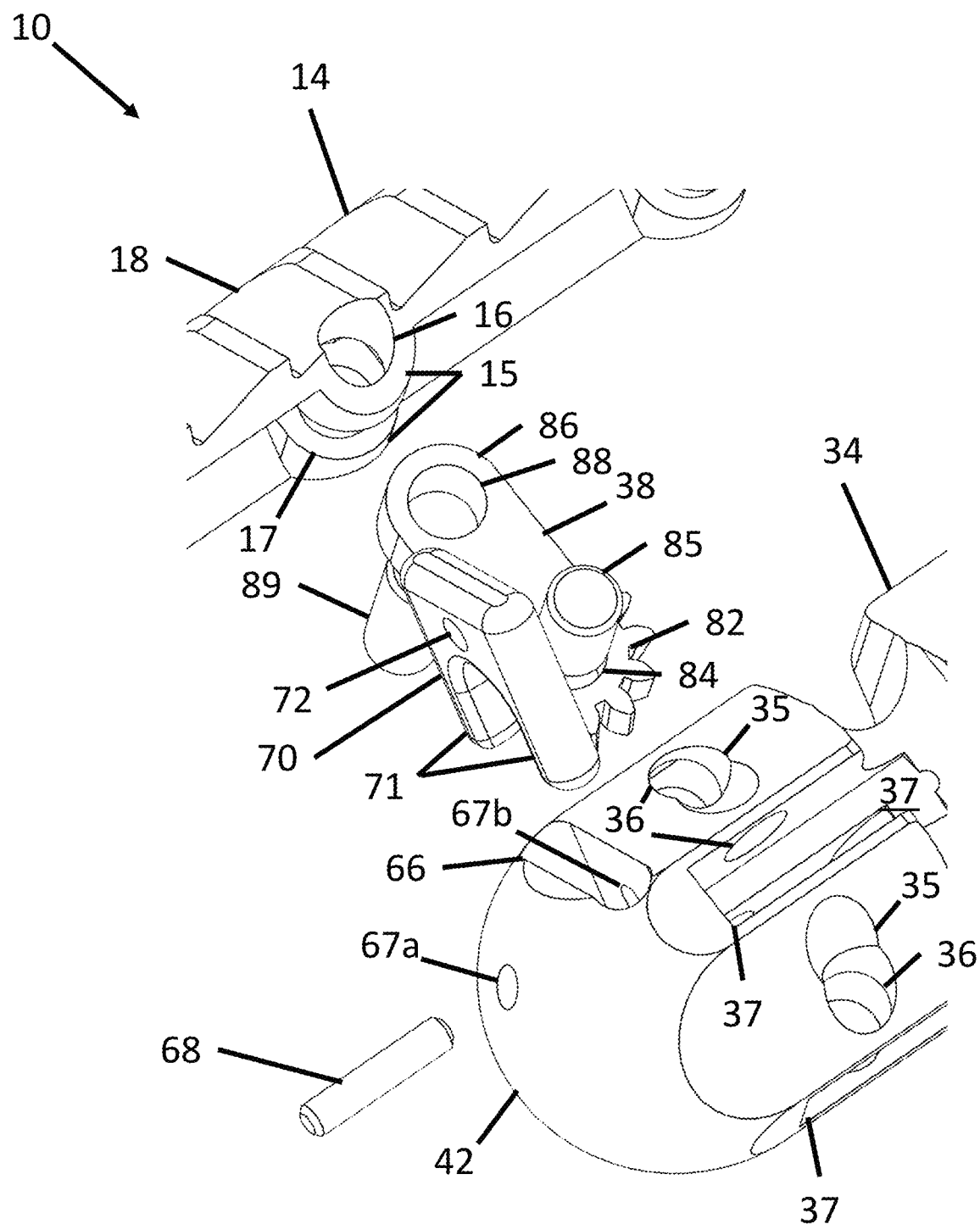
FIG. 3 is an exploded view of a portion of the implant of FIG. 1A.

Turning to FIG. 3, the shuttle 34 includes one axially extending slot 37 per link 38 in the implant 10 (only two slots 37 being visible in FIG. 3), and the slots 37 are dimensioned to receive the links 38. The slots 37 are arranged in two groups, each group extending around a circumference of the shuttle 34 and being aligned with one of the threaded regions 74, 78 of the shaft 46. Between each circumferentially adjacent pair of slots is an 8-shaped opening 35 that branches to two pinholes 36. Each pinhole 36 extends to a lateral face of a slot 37. The shuttle end 82 of any link 38 can be pivotably connected to the shuttle 34 by inserting the shuttle end 82 into the slot 37, aligning a shuttle end cylindrical hole 84 of the shuttle end 82 with the pinholes 36 ending on the slot 37, and inserting a shuttle end pin 85 through one of the openings 35 until the shuttle end pin 85 extends through the shuttle end hole 84. The shuttle end pin 85 may be pushed until it extends partially into two pinholes 36, or until it is centered within the shuttle end hole 84.

Each endplate 14 includes a pair of tabs 15 per link 38 to be connected to the endplate 14 (only one pair of tabs 15 of one endplate 14 being visible in FIG. 3). Each pair of tabs 15 defines a gap 17 therebetween that is dimensioned to receive an endplate end 86 of a link 38. Each tab 15 includes a track 16 having a generally circular cross section extending from a lateral side of the tab 15 to the gap 17. The endplate end 86 of any link 38 may therefore be pivotably connected to the endplate 14 by inserting the shuttle end 86 into the gap 17, aligning an endplate end cylindrical hole 88 with the tracks 16 ending on the gap 17, and inserting an endplate end pin 89 through one of the tracks 16 until the endplate end pin 89 extends through the endplate end hole 88. The endplate end pin 89 may be pushed until it extends partially into two tracks 16, or until it is centered within the endplate end hole 88.

The clip 70 includes arms 71 and a first aperture 72. The channel 66 is deep enough to accommodate the arms 71 such that the clip 70 may be inserted into the channel 66 until the first aperture 72 is aligned with a second aperture 67a extending from a distal opening in the dome 42 to the channel 66 and a third aperture 67b extending proximally from the channel 66. The clip 70 can then be locked in place by inserting a dowel 68 through the second aperture 67a into the first aperture 72 and, optionally, into the third aperture 67b. Assembling the implant 10 can include inserting the shaft 46 (not shown in FIG. 3) into the shuttle 34 from the shuttle's 34 proximal end, dropping the clip 70 into the channel 66 such that the arms 71 seat within the neck 62 of the shaft 46, then locking the clip 70 in place by inserting the dowel 68 through the second aperture 67a into the first aperture 72 and, optionally, the third aperture 67b.

Though the implant 10 shown in FIGS. 1A-3 includes four endplates and has a generally square axial cross-section in the closed position, multiple arrangements are contemplated. In other arrangements, the implant 10 includes more or fewer endplates 14. In further arrangements, the endplates 14 in any number are shaped and arranged to provide the implant 10 in the closed position with other axial cross-sectional shapes, such as, for example, shapes that are generally circular, oblong, obround, or generally in the shape of a polygon other than a square.

Figure 4A:
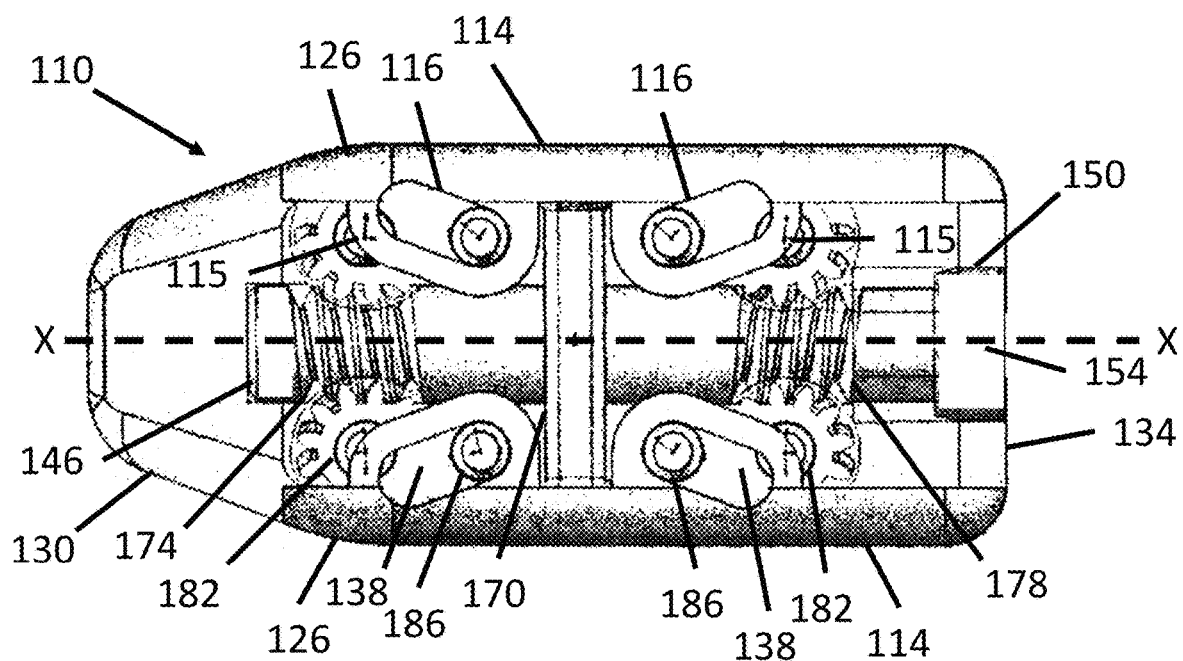
FIG. 4A is a side elevation view of an implant according to a second arrangement in a closed position.
Figure 4B:
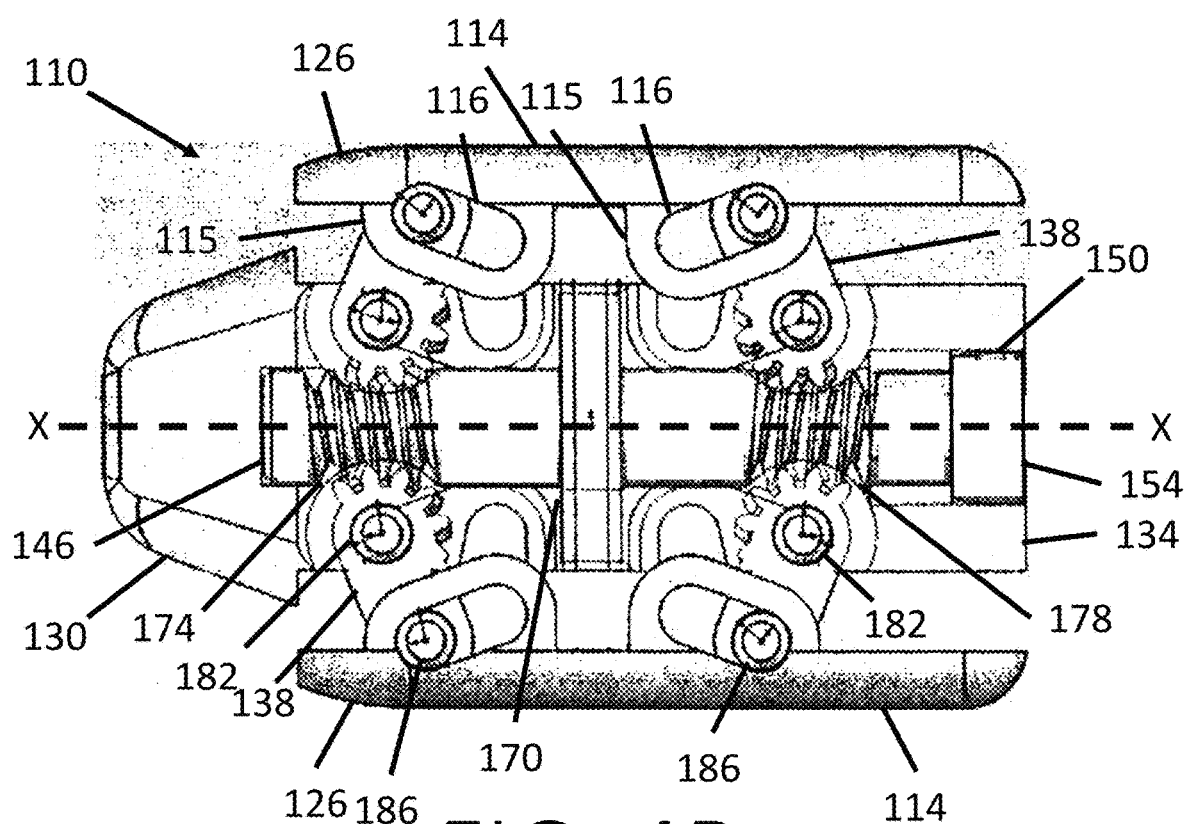
FIG. 4B is a side elevation view of the implant of FIG. 4A in an open position.

Turning to FIGS. 4A and 4B, an implant 110 according to another embodiment includes two opposed endplates 114 on opposite sides of a shuttle 134. A shaft 146 extends within the shuttle 134 along a central axis X. The shaft 146 is rotatable about the central axis X, but is prevented from translating relative to the shuttle 134 by a collar 170 that may engage a neck (not shown) in the shaft 146. The shaft 146 includes a first threaded region 174 and a second threaded region 178. The first threaded region 174 and the second threaded region 178 are both worm threaded, but the first threaded region 174 and second threaded region 178 are worm threaded in opposite directions. In the illustrated arrangement, a flared end 150 provides a proximal end of the shaft 146, but in other arrangements the proximal end of the shaft 146 is of equal or lesser diameter than an adjoining part of the shaft 146. The proximal end of the shaft 146 includes a drivable feature 154, which is a recess having teeth for engaging with a driving tool. In other arrangements, the drivable feature 154 is a toothed protrusion or any other rotatably drivable element. The drivable feature 154 is accessible from a proximal end of the implant 110.

The endplates 114 are moveable between a closed position shown in FIG. 4A and an open position shown in FIG. 4B. Though not shown in the figures, the endplates 114 may include ridged exterior surfaces similar to those indicated with numeral 18 in FIG. 1. In the illustrated example, distal ends of the endplates 114 include distal portions 126 that taper to meet a rounded nose 130 extending from a distal end of the shuttle 134 such that the distal portions 126 are flush with the nose 130 when the implant 110 is in the closed position. Each endplate 114 include tabs 115 extending toward the opposite endplate 114, and each tab 115 includes an elongate track 116 extending there along.

Links 138 connect the shuttle 134 to the endplates 114. In the illustrated arrangement, two links 138 connect to each endplate 114, though more or fewer links 138 can be connected to each endplate 114 in other arrangements. Each link 138 includes a shuttle end 182 connected to the shuttle 134 such that the shuttle end 182 may rotate, but not translate, relative to the shuttle 138. The shuttle ends 182 include gear teeth extending radially outward therefrom and engaging with the threaded regions 174, 178 of the shaft 146. The gear teeth of the shuttle ends 182 of the illustrated arrangement are helical, and therefore extend transverse to pivot axes 182 of their respective shuttle ends 182, but in other arrangements the gear teeth may be parallel to the pivot axes of their respective shuttle ends 182. Each link 138 also includes an endplate end 186 connected to a tab 115 such that the endplate end 186 can rotate within and slide along the track 116 of the tab 115. The two links 138 connected to each endplate 114 extend in opposite directions from their respective shuttle ends 182 in the closed position. In the illustrated arrangement, the relatively distally located links 138 that are in geared engagement with the first threaded region 174 extend proximally from their shuttle ends 182 when the shuttle 110 is in the closed position, and the relatively proximally located links 138 that are in geared engagement with the second threaded region 178 extend distally from their shuttle ends 182 when the implant 110 is in the closed position. Therefore, in the illustrated arrangement, each link 138 extends from its respective shuttle end 182 toward the collar 170 when the implant 110 is in the closed position. However, in other arrangements, the links 138 may all extend away from the collar 170 from their respective shuttle ends 182 when the implant 110 is in the closed position such that the relatively distal links 138 in geared engagement with the first threaded region 174 extend distally away from their shuttle ends 182 and the relatively proximal links 138 in geared engagement with the second threaded region 174 extend proximally from their shuttle ends 182.

Because the threaded regions 174, 178 are threaded in opposite directions from one another, rotation of the shaft 146 will cause the two links 138 connected to any one endplate 114 to rotate in opposite directions with respect to one another. For example, from a given perspective, rotating the shaft 146 in one direction will cause one link 138 connected to a given endplate 114 to rotate clockwise while causing the other link 138 connected to the same endplate 114 to rotate counterclockwise. Because the two links 138 attached to any endplate 114 are disposed to extend in opposite directions from their respective shuttle ends 182 when the shuttle 110 is in the closed position, rotating the shaft 146 causes the endplate ends 186 of the two links 138 connected to any endplate 114 to travel simultaneously either toward or away from each other and either toward or away from the central axis X. Further, because the endplate ends 186 of the links 138 are free to travel along the tracks 116 of the endplates 114, the shapes of the tracks 116 guide travel of the endplates 114 as the implant 110 transitions between the open and closed positions. In the illustrated arrangement, the two links 138 connected to either endplate 114 are connected to extend at opposite but equal, or at least substantially equal, angles relative to the central axis X throughout the transition from the open position to the closed position, as are the two tracks 116 of either endplate 114. As a result, transitioning between the open and closed positions by rotation of the shaft 146 in either direction causes both endplates 114 to translate only perpendicularly to the central axis X without rotating or translating parallel to the central axis X. Transitioning between the open and closed positions therefore only includes expansion or contraction of the implant 110 in one dimension.

In some arrangements, additional structure may be provided to guide the movement of the endplates 114 such that their travel between the open and closed positions is only perpendicular to the central axis X, without rotation. For example, one or more vertical rails may be connected to corresponding tracks of both endplates to constrain the movement of the endplates 114 along the vertical direction of the rails. Such vertical rail(s) may also be coupled to the shuttle 134. In some implementations, such vertical guidance may be provided by the collar 170. That is, one or more portions of the collar 170 may extend from the shuttle 134 and engage such tracks of the endplates 114.

In various other arrangements, the implant 110 includes more or fewer endplates 114 or endplates of other configurations, and therefore has different characteristics through the transition between the open and closed positions. In some arrangements, the implant 110 includes only one endplate 114. In others, the implant 110 incudes 3 or more endplates 114 each configured to expand away from the central axis X as the implant 110 transitions from the closed position to the open position. In further arrangements, one or more of the endplates 114 have differently arranged tracks 116 that result in rotation, translation along the central axis X, or both, of the endplates 114 as the implant 110 transitions from the closed position to the open position. In yet further arrangements, the implant 110 includes more than 2 endplates 114 at equal circumferential and angular distribution around the central axis X.

Though two distinct implants 10, 110 are shown in FIGS. 1A-3 and FIGS. 4A and 4B, respectively, it should be understood that the differing features and ideas of the two implants are generally intercombinable. For example, in some arrangements, an implant has endplates providing a generally continuous capsule shape from a nose to a proximal end of the endplates while the implant is in a closed position, and the endplates travel only perpendicularly to a central axis of the implant as the implant transitions from the closed position to an open position.

In one or more alternative embodiments, rather than simply translating perpendicularly to the central axis X, the endplates 114 may also translate by different amounts at their respective distal and proximal ends, such that the endplates 114 are angled obliquely to the central axis X in the open position. Such embodiments might be particularly useful, for example, for correcting or maintaining a desired lordosis. Such embodiments may be implemented by, for example, making at least one of the links 38, 138 longer than others. In one example, all of the links 38, 138 towards the distal end of the implant 10, 110 that are driven by threaded regions 74, 174 may be longer than the links 38, 138 towards the proximal end of the implant 10, 110 that are driven by threaded region 78, 178. As a result, the endplates 114 may be further spaced apart from one another at their distal ends than at their proximal ends. To avoid over constraining the implant 10, 110, at least one link 38, 138 per endplate 14, 114 is connected to the endplate 14, 114 at an elongated track 116 as shown in FIGS. 4A and 4B.

In one or more other embodiments, the links 38, 138 towards the distal end of the implant 10, 110 may be actuated independently of the links 38, 138 towards the proximal end of the implant 10, 110. Such embodiments might be particularly useful, for example, for customizing a desired amount of lordosis to be imposed between the adjacent vertebrae. Such embodiments might be implemented by, for example, dividing the shaft 46, 146 along the central axis X into two independently rotatable shaft sections (i.e., into a distal shaft section and a proximal shaft section), where the distal shaft section includes the distal threaded region 74, 174 and the proximal shaft section includes the proximal threaded region 78, 178. Such independently rotatable shaft sections could be independently actuatable. For example, the shaft sections could be concentrically arranged in the same manner as the two-part worm disclosed in connection with FIG. 10A of U.S. Pat. No. 8,303,663 ("the '663 Patent"), the entire disclosure of which is hereby incorporated herein by reference. That is, a post extending proximally from the distal shaft section along the central axis X can be received coaxially within the proximal shaft section (which may be hollow). The proximal end of that post could then be actuated independently of the proximal shaft section, such as by providing independent drivable features. For example, the proximal end of the post connected to the distal shaft section could include a recess having an internal profile (e.g., with teeth) for engaging a complementary portion of a first driving tool, and the proximal end of the proximal shaft section could include an outer profile having features (e.g., splines) for engaging a complementary portion of an independently actuatable part of the first driving tool or a complementary portion of a separate second driving tool.

Although the concept herein has been described with reference to particular embodiments, it is to be understood that these embodiments are merely illustrative of the principles and applications of the present disclosure. It is therefore to be understood that numerous modifications may be made to the illustrative embodiments and that other arrangements may be devised without departing from the spirit and scope of the present disclosure as defined by the appended claims.

The invention claimed is:

1. A spinal interbody implant comprising:
   a shaft extending along and rotatable about a central axis, the shaft including a first threaded region;

a first link having a first end and an opposite second end, the first end of the first link having first gear teeth directly engaged to the first threaded region such that the first end of the first link is rotatable about a first point by rotating the shaft about the central axis, the first point having a fixed location relative to the central axis, and the fixed location of the first point being positioned at a first longitudinal dimension defined along the central axis;

a second link positioned on an opposite side of the central axis of the shaft from the first link, the second link having a first end and an opposite second end, the first end of the second link having second gear teeth directly engaged to the first threaded region such that the first end of the second link is rotatable about a second point by rotating the shaft about the central axis, the second point having a fixed location relative to the central axis, the fixed location of the second point being positioned at the same first longitudinal dimension along the central axis as the fixed location of the first point; and a plurality of endplates including a first endplate connected to the second end of the first link at a first connection location and including a second endplate connected to the second end of the second link at a second connection location, wherein the endplates among the plurality of endplates are movable between a closed position of the implant and an open position of the implant, and wherein the endplates are further from the central axis and each other when in the open position than when in the closed position, wherein the first and second gear teeth are directly engaged to the threaded region such that an amount of rotation of the shaft induces the first endplate at the first connection location and the second endplate at the second connection location to move away from the central axis by symmetrical distances in opposite directions away from the central axis.

2. The spinal interbody implant of claim 1, wherein the shaft includes a second threaded region located at a different position along the central axis than the first threaded region; and wherein the implant includes a third link having a first end having third gear teeth directly engaged to the second threaded region such that the first end of the third link is rotatable about a third point by rotating the shaft about the central axis.

3. The spinal interbody implant of claim 2, wherein, in the closed position, the first link and the third link each extend in generally the same direction relative to the central axis.

4. The spinal interbody implant of claim 3, wherein the first, second, and third links extend proximally away from their first ends in the closed position.

5. The spinal interbody implant of claim 3, wherein the first, second, and third links extend perpendicularly relative to the central axis in the open position.

6. The spinal interbody implant of claim 1, comprising a shuttle, wherein the shaft is nontranslatably retained within a cavity of the shuttle, and wherein the first end of the first link is fixed to the shuttle.

7. The spinal interbody implant of claim 6, wherein the plurality of endplates contact the shuttle when in the closed position and are spaced apart from the shuttle when in the open position.

8. The spinal interbody implant of claim 7, wherein the endplates are located at a different location along the central axis in the open position than in the closed position.

9. The spinal interbody implant of claim 7, wherein the endplates are equally spaced around the central axis in both the open position and the closed position.

10. The spinal interbody implant of claim 7, wherein the endplates meet in the closed position to form a rounded nose at a distal end of the implant.

11. The spinal interbody implant of claim 10, wherein the endplates meet in the closed position to form a generally enclosed capsule shape from a distal tip of the nose to proximal ends of the endplates.

12. A spinal interbody implant comprising:

a shuttle extending along a central axis;

a first plurality of links each being connected at a geared first end to the shuttle at a fixed location relative to the central axis, and each of the first plurality of links having a second end opposite to the respective first end;

a second plurality of links each being connected at a geared first end to the shuttle at a fixed location relative to the central axis, and each of the second plurality of links having a second end opposite to the respective first end;

a plurality of endplates spaced circumferentially around the central axis and the shuttle, each of the plurality of endplates being connected to the second end of at least one link of the first plurality of links and to the second end of at least one link of the second plurality of links; and a shaft disposed within the shuttle and along the central axis, the shaft including a first threaded region in direct geared engagement with the first ends of the first plurality of links, and the shaft including a second threaded region in direct geared engagement with the first ends of the second plurality of links;

wherein the first plurality of links are drivable by rotation of the shaft to transition the implant from a closed position to an open position by causing the endplates among the plurality of the endplates to move away from the central axis, wherein the first plurality of links extend at a greater angle relative to the central axis in the open position than in the closed position, and wherein an amount of rotation of the shaft induces the second ends of the first plurality of links to move away from the central axis by symmetrical distances in opposite directions away from the central axis.

13. The spinal interbody implant of claim 12, wherein the endplates extend at the same angle relative to the central axis when in the open position as when in the closed position.

14. The spinal implant of claim 12, wherein the second ends of the first plurality of links are farther from the second ends of the second plurality of links in the open position than in the closed position.

15. The spinal implant of claim 12, wherein the endplates include elongate tracks and the second ends of the first plurality of links are translatably connected to the endplates within the tracks.

16. A method of treating a spinal injury, the method comprising: inserting an implant between two vertebrae, the implant including:

a shaft extending along a central axis, the shaft including a first threaded region;

a first link having a first end and an opposite second end, the first end of the first link having first gear teeth engaged to the first threaded region such that the first end of the first link is rotatable about a first point by rotating the shaft about the central axis, the first point having a fixed location relative to the central axis, and the fixed location of the first point being positioned at a first longitudinal dimension defined along the central axis;

a second link having a first end and an opposite second end, the first end of the second link having second gear teeth engaged to the first threaded region such that the first end of the second link is rotatable about a second point by rotating the shaft about the central axis, the second point having a fixed location relative to the central axis, and the fixed location of the second point being positioned at the same first longitudinal dimension along the central axis as the fixed location of the first point; and a plurality of endplates including a first endplate connected to the second end of the first link at a first connection location and including a second endplate connected to the second end of the second link at a second connection location; and causing endplates among the plurality of endplates to translate away from the central axis and each other by rotating the shaft so as to induce the first endplate at the first connection location and the second endplate at the second connection location to move away from the central axis by symmetrical distances in opposite directions away from the central axis.

* * * * *